United States Patent [19]

Shimazaki et al.

[11] 4,411,997

[45] Oct. 25, 1983

[54] METHOD FOR PRODUCING L-LYSINE BY FERMENTATION

[75] Inventors: Keishi Shimazaki; Yoshihiro Nakamura; Yasutsugu Yamada, all of Saga, Japan

[73] Assignee: Ajinomoto Company Incorporated, Tokyo, Japan

[21] Appl. No.: 333,455

[22] Filed: Dec. 22, 1981

[30] Foreign Application Priority Data

Dec. 29, 1980 [JP] Japan .................................. 55-185676

[51] Int. Cl.³ ...................... C12P 13/08; C12N 15/00; C12N 1/20; C12R 1/13; C12R 1/15
[52] U.S. Cl. .................................... 435/115; 435/840; 435/843; 435/172; 435/253
[58] Field of Search ............... 435/115, 840, 843, 172, 435/253

[56] References Cited

U.S. PATENT DOCUMENTS

| | | | |
|---|---|---|---|
| 2,979,439 | 4/1961 | Kinoshita et al. | 435/115 |
| 3,707,441 | 12/1972 | Shiio et al. | 435/115 |
| 3,708,395 | 1/1973 | Nakayama et al. | 435/115 |
| 3,825,472 | 7/1974 | Kubota et al. | 435/115 |
| 4,169,763 | 10/1979 | Nakayama et al. | 435/115 |
| 4,275,157 | 6/1981 | Tosaka et al. | 435/115 |

*Primary Examiner*—Lionel M. Shapiro
*Attorney, Agent, or Firm*—Oblon, Fisher, Spivak, McClelland & Maier

[57] ABSTRACT

A method for producing L-lysine by fermentation, which comprises, culturing aerobically in a culture medium a mutant of the genus Brevibacterium or Corynebacterium which is resistant to ethylene glycol and capable of producing L-lysine, and recovering the L-lysine which accumulates in the culture medium.

7 Claims, No Drawings

METHOD FOR PRODUCING L-LYSINE BY FERMENTATION

BACKGROUND OF THE INVENTION

1. Field of the Invention

The present invention relates to a method for producing L-lysine by fermentation.

2. Description of the Prior Art

L-lysine, which is used as a feedstuff is normally produced industrially by a fermentation process in which L-lysine producing mutants of the genus Brevibacterium or Corynebacterium are used. Various L-lysine-producing mutants, produced by the artificial mutation of wild strains of microorganisms of the genera Brevibacterium and Corynebacterium, are known. Examples of such artificial mutants are mutants resistant to S-(2-aminoethyl)-cystein (hereinafter identified as AEC), mutants requiring L-amino acids such as L-homoserine, L-threonine, L-leucine, or L-methionine for their growth (Japanese Published Examined Patent Application Nos. 28078/1963, 26639/1977, 28677/1973, U.S. Pat. Nos. 3,707,441 2,979,439), mutants resistant to AEC and further requiring an amino acid such as L-leucine, L-homoserine, L-proline, L-serine, L-arginine, L-alanine or L-valine (Japanese Published Examined Patent Application Nos. 36888/1974, 210787/1976, 34836/1979, 1040/1980, U.S. Pat. Nos. 3,708,395 and 3,825,472), L-lysine-producing mutants resistant to $\alpha$-amino-lauryllactam, aspartic acid-analogs, sulfa drugs, quinoids, N-lauroyl leucine, or to inhibitors of oxalacetate, decarboxylase or respiratory system enzymes (Japanese Published Unexamined Patent Application Nos. 31093/1975, 102498/1977, 9394/1978. 86089/1978, 9783/1980, 9759/1980, 32995/1981, 39778/1981, Japanese Published Examined Patent Application Nos. 43591/1978, 1833/1978), l-lysine-producing mutants requiring inositol or acetic acid (Japanese Published Unexamined Patent Application Nos. 9784/1980, 8692/1981), and L-lysine-producing mutants sensitive to fluoropyruvic acid or to a temperature more than 34° C. (Japanese Published Unexamined Patent Application Nos. 9783/1980, 86090/1978). A need continues to exist, however, for a method by which L-lysine can be produced in greater yields by fermentative techniques.

SUMMARY OF THE INVENTION

Accordingly, one object of the present invention is to provide a method of preparing L-lysine in improved yields by fermentation processes.

Briefly, this object and other objects of the present invention as hereinafter will become more readily apparent can be attained in a method for producing L-lysine by fermentation by aerobically culturing a mutant of the genus Brevibacterium or Corynebacterium which is resistant to ethylene glycol and recovering the L-lysine produced.

DETAILED DESCRIPTION OF THE PREFERRED EMBODIMENTS

It has now been found that the production of L-lysine can be increased when resistance to ethylene glycol is imparted to known L-lysine producing microorganisms of the genus Brevibacterium or Corynebacterium.

The microorganisms employed in the present invention are mutants which belong to the genus Brevibacterium or Corynebacterium. The mutants have the characteristics necessary for the production of L-lysine which are the homoserine requirement, resistance to AEC and resistance to $\alpha$-chloro-caprolactam (CCL). Of course, the mutants possess resistance to ethylene glycol. Representative mutant specimens of the present invention are:

| Brevibacterium lactofermentum | AJ 11657 FERM-P 5838 FERM-BP 77(AEC$^r$, CCL$^r$, Ala$^-$, EG$^r$) |
|---|---|
| Brevibacterium flavum | AJ 11658 FERM-P 5839 FERM-BP 78 (Hse$^-$, EG$^r$) |
| Corynebacterium acetoglutamicum | AJ 11656 FERM-P 5837 FERM-BP 76(AEC$^-$, Ala, EG$^-$) | wherein the abbreviations in parenthesis have the following meanings:

AEC$^r$: resistance to S-(2-aminoethyl)-L-cystein
CCL$^r$: resistance to $\alpha$-chlorocaprolactam
Hse$^-$: requirement of L-homoserine for growth
EG$^r$: resistance to ethylene glycol
Ala$^-$: requirement of L-Alanine for growth.

The mutants identified above by FERM-BP numbers were originally deposited with the FERM-P numbers on Dec. 27, 1980 at the Fermentation Research Institute, Agency of Industrial Sciences and Technology, Ministry of International Trade and Industry (FRI), 1-3, Higashi 1-chome, yatabe-machi, Tsukuba-gun, Ibaragi-ken 305, Japan and these deposits were converted to deposits under the Budapest Treaty on Dec. 9, 1981 with FRI which has aquired the status of an International Depository Authority as of May 1, 1981.

The mutants mentioned above can be induced from parent microorganism strains by any conventional method. The first step of induction is to mutate the parent strains with a suitable chemical mutagen such as N-methyl-N'-nitro-N-nitrosoguanidine (hereinafter referred to as NG) and nitrous acid or with irradiation by ultraviolet light. The second step of the process is to select resistant mutants by picking-up colonies of microorganisms on plates of a nutrient agar medium containing an amount of ethylene glycol which inhibits the growth of the parent strains. Thereafter, the mutants are evaluated for L-lysine productivity by a standard method.

The ethylene glycol resistant mutants are almost resistant to concentrated aqueous solutions of sodium chloride, potassium chloride, ammonium chloride, ammonium sulfate, potassium sulfate, sodium sulfate, glucose, fructose, sucrose, and maltose which inhibit the growth of the parent strains.

Suitable parent strains from which the present mutants can be produced include mutants capable of producing L-lysine and wild strains of the genus Brevibacterium or Corynebacterium. When wild strains are used, L-lysine productivity is imparted to the wild strains prior to or after imparting resistance to ethylene glycol to the wild strains. In order to impart L-lysine productivity to the microorganisms, as is known, resistance to AEC must be imparted or the mutant must possess the homoserine growth requirement.

The preferred wild strains of the genus Brevibacterium or Corynebacterium are coryne-form glutamic acid producing bacteria and the examples include:

| Brevibacterium divaricatum | ATCC 14020 |
|---|---|
| Brevibacterium flavum | ATCC 14067 |
| Brevibacterium lactofermentum | ATCC 13869 |

-continued

| | |
|---|---|
| Brevibacterium sascharolyticum | ATCC 14066 |
| Corynebacterium acetoacidophilum | ATCC 13870 |
| Corynebacterium glutamicum | ATCC 13032 |
| Corynebacterium acetoglutamicum | ATCC 15086 |

The method by which mutants within the scope of the present invention can be induced and the degree of resistance to ethylene glycol are shown in Experiments 1 and 2.

EXPERIMENT 1

*Brevibacterium lactofermentum* AJ 11082 FERM-P 3840 NRRL-B 11470 (AEC$^r$, CCL$^r$, Ala$^-$) which was derived from *B. lactofermentum* ATCC 13869 was cultured on a nutrient agar medium at 30° C. for 24 hours. The cells which grew on the agar medium were scraped together and suspended in sterilized water containing 250 mg/ml NG and the suspension was allowed to stand at 30° C. for 30 minutes. The microbial cells thus treated were washed with phosphate buffer solution, inoculated on a plate of the minimum culture medium of which the composition is given in Table 1 containing 30 g/dl ethylene glycol, and cultured at 30° C. with shaking for 2 to 4 days until ethylene glycol resistant mutants propagated in the culture medium. Then the culture medium was spread on the agar plates of the minimum culture medium and the plates were incubated at 30° C. for 4 days.

TABLE 1

Composition of Minimum Medium (pH 7.2)

| Component | Conc. | Component | Conc. |
|---|---|---|---|
| Glucose | 2.0 g/dl | MnSO$_4$.4H$_2$O | 1.0 mg/dl |
| Urea | 0.25 g/dl | L-Alanine | 50 mg/dl |
| Ammonium sulfate | 1.0 g/dl | Nicotinamide | 0.5 mg/dl |
| KH$_2$PO$_4$ | 0.1 g/dl | Biotin | 5.0 mg/dl |
| MgSO$_4$.7H$_2$O | 0.04 g/dl | Thiamine.HCl | 10 mg/dl |
| FeSO$_4$.7H$_2$O | 1.0 mg/dl | Sodium chloride | 50 mg/dl |

After the cultivation, the colonies which turned up as ethylene glycol resistant mutants were evaluated for L-lysine productivity. It was found that the mutants capable of producing more L-lysine than the parent strain were obtained with high frequency, and *B. lactofermentum* AJ 11657 FERM-P 5838 FERM-BP which was found to produce more L-lysine than any other mutant was selected.

Other mutants that were prepared which are within the scope of the present invention include *C. acetoglutamicum* AJ 11656 and *B. flavum* AJ 11658. These mutants were obtained by the same culturing process.

EXPERIMENT 2

Three ml portions of the minimum medium of Table 1 further containing ethylene glycol of a concentration shown in Table 2 were poured into small size test tubes and were sterilized.

Test strains were washed with the minimum medium and inoculated into the mediums in the test tubes. Then the tubes were incubated at 30° C. for 24 hours with shaking. After the cultivation, the growth of each strain was determined by measuring the optical density at 562 nm of the culture broths. The results are shown in Table 2. The degree of resistance to ethylene glycol is represented by the relative values of the growth to the control.

TABLE 2

| Conc. of E.G. (%) | AJ 11082 | AJ 11657 | AJ 11094 | AJ 11656 | AJ 11275 | AJ 11658 |
|---|---|---|---|---|---|---|
| 0 | 100 | 100 | 100 | 100 | 100 | 100 |
| 5 | 70 | 100 | 80 | 100 | 70 | 100 |
| 10 | 40 | 90 | 40 | 85 | 50 | 100 |
| 15 | 0 | 70 | 10 | 60 | 20 | 80 |
| 20 | 0 | 50 | 0 | 40 | 0 | 50 |
| 30 | 0 | 10 | 0 | 10 | 0 | 10 |

The mutants were cultured aerobically in a conventional culture medium containing carbon sources, nitrogen sources, and inorganic ions, and when required, minor nutrients. Suitable carbon sources include saccharides such as glucose, fructose, and sucrose, and molasses and hydrolyzed starch containing these saccharides; organic acids such as acetic acid, and propionic acid; and alcohols, which are preferably used. Suitable nitrogen sources include, for example, ammonium sulfate, gaseous ammonia and urea.

Cultivation is carried out preferably under aerobic conditions, for 2 to 7 days at a temperature ranging from 24° to 37° C. with preferable adjustment of the pH of the culture medium to 5.0 to 9.0 with an organic or inorganic acid or alkali. For this purpose, urea, CaCO$_3$, and gaseous ammonia may be used.

The L-lysine which accumulates in the culture medium may be recovered by an entirely conventional recovery technique such as those which use an ion-exchange resin.

Having generally described this invention, a further understanding can be obtained by reference to certain specific examples which are provided herein for purpose of illustration only and are not intended to be limiting unless otherwise specified.

EXAMPLE 1

Twenty ml portions of Culture medium A, having the composition shown in Table 3 were placed into 500 ml-flasks which were than heated at 110° C. for 5 minutes for sterilization. Thereafter, the contents of each flask were supplemented with 1.0 g CaCO$_3$ separately sterilized.

TABLE 3

Composition of Culture Medium

| Component | conc. | A | B | C | D |
|---|---|---|---|---|---|
| Glucose | (g/dl) | 15 | 1.5 | 2.0 | 15* |
| Ammonium sulfate | (g/dl) | 4.5 | — | — | 4.5 |
| Ammonium acetate | (g/dl) | — | 0.3 | 0.5 | — |
| Urea | (g/dl) | — | 0.1 | 0.2 | — |
| KH$_2$PO$_4$ | (g/dl) | 0.1 | 0.1 | 0.1 | 0.1 |
| MgSO$_4$.7H$_2$O | (g/dl) | 0.04 | 0.04 | 0.04 | 0.04 |
| FeSo$_4$.7H$_2$O | (mg/dl) | 1.0 | 1.0 | 1.0 | 1.0 |
| MnSO$_4$.4H$_2$O | (mg/dl) | 1.0 | 1.0 | 1.0 | 1.0 |
| Biotin | (μg/dl) | 5.0 | 5.0 | 5.0 | 5.0 |
| Thiamine.HCl | (μg/dl) | 20 | 20 | 5.0 | 20 |
| Nicotinamide | (μg/dl) | — | — | 0.1 | — |
| Soy protein hydrolyzed | (TN 7%, ml/dl) | 1.5 | 2.0 | 3.0 | 1.5 |
| pH | | 7.0 | 7.5 | 7.2 | 7.0 |

*Beet molasses is employed as the carbon source

Each strain for testing shown in Table 5 which was previously cultured on a bouillon agar slant was inoculated into a batch of culture medium, and cultured with shaking at 31° C. for 72 hours. After the cultivation, the determination of the L-lysine which accumulated in each broth culture was conducted colorimetrically and the results are shown in Table 4.

TABLE 4

| Strain | L-lysine accumulated (as L-lysine.HCL) g/dl | Yield % |
|---|---|---|
| AJ 11802 | 5.0 | 33 |
| AJ 11657 | 6.0 | 40 |
| AJ 11094 | 4.4 | 29 |
| AJ 11656 | 5.1 | 34 |
| AJ 11275 | 4.2 | 28 |
| AJ 11658 | 5.3 | 35 |

A culture broth of AJ 11656 prepared in the same manner as described above was collected and centrifuged to remove microbial cells, and the solid $CaCO_3$. 1.0 liter supernatant solution thus obtained was passed through a column of "Amberlite IR-120" in the acid form. By this procedure L-lysine was adsorbed on the resin, and it was eluted with 3% ammonia water. The eluate was evaporated and the concentrated solution was cooled to a temperature low enough to crystallize L-lysine, and 36.7 g L-lysine.HCl. 2aq crystal was obtained.

EXAMPLE 4

A fifty ml portion of Culture medium B, whose composition is given in Table 3, was placed in a 500 ml flask and heated at 110° C. for 4 minutes for sterilization. Then the culture broth was inoculated with B. lactofermentum AJ 11657 which had been been grown on a bouillon agar slant. The inoculated medium was cultured at 31° C. for 18 hours with shaking to prepare a seed culture broth.

At three hundred ml portion of Culture medium C in Table 3 was placed in a 1.0 liter-fermentation vessel and heated for sterilization. The medium was inoculated with 15 ml of a seed culture broth and cultivation was conducted at 31° C. with agitation and aeration. During the cultivation the pH of the medium was maintained in the range from 7.2 to 8.0 with addition of a solution containing acetic acid and ammonium acetate.

After 55 hours of cultivation, the L-lysine which had accmulated in the culture broth was determined and the results obtained are shown in Table 5.

TABLE 5

| Strain No. | L-lysine accumulated (as lysine.HCl) | (%) |
|---|---|---|
| AJ 11657 | 8.5 g/dl | 32 |
| AJ 11082 (parent) | 7.2 g/dl | 29 |

EXAMPLE 3

Twenty ml portions of Culture medium D were placed in 500 ml flasks and heated at 110° C. for 5 minutes. Each flask was supplemented with 1.0 g $CaCO_3$ separately sterilized.

Each strain listed in Table 6, which had been previously cultured on a bouillon agar slant, was inoculated into a batch of the culture medium and cultured at 31° C. for 72 hours with shaking. After the cultivation, the L-lysine which had accumulated in the culture broth samples was determined and the results are shown in Table 6.

TABLE 6

| Strain No. | L-lysine accumulated (as lysine.HCl) | Yield |
|---|---|---|
| AJ 11082 | 4.8 (g/dl) | 32 (%) |
| AJ 11657 | 5.6 | 37 |
| AJ 11094 | 4.1 | 27 |
| AJ 11656 | 4.7 | 31 |
| AJ 11275 | 4.2 | 28 |
| AJ 11658 | 4.8 | 32 |

Having now fully described this invention, it will be apparent to one of ordinary skill in the art that many changes and modifications can be made thereto without departing from the spirit or scope of the invention as set forth herein.

What is claimed as new and desired to be secured by Letters Patent of the United States is:

1. A method for producing L-lysine by fermentation, which comprises: culturing aerobically in a culture medium a mutant of the genus Brevibacterium or Corynebacterium which is resistant to ethylene glycol and capable of producing L-lysine; and recovering the L-lysine which accumulates in the culture medium.

2. The method of claim 1, wherein said mutant belongs to the species Brevibacterium lactofermentum, Brevibacterium flavum or Corynebacterium acetoglutamicum.

3. The method of claim 1, wherein said mutant is resistant to S-(2-aminoethyl) L-cystein.

4. The method of claim 1, wherein said mutant requires L-homoserine for its growth.

5. The method of claim 1, wherein said mutant is derived from a parent species of bacterium selected from the group consisting of Brevibacterium divaricatum, Brevibacterium flavum, Brevibacterium lactofermentum, Brevibacterium saccharolyticum, Corynebacterium acetoacidophilum, Corynebacterium glutamicum and Corynebacterium acetoglutamicum.

6. A biologically pure culture of a mutant of the genus Brevibacterium resistant to ethylene glycol selected from the group consisting of Brevibacterium lactofermentum AJ 11657, FERM-P 5838, FERM-BP ($AEC^r$, $CCL^r$, $ALa^-$, $EG_r$) and Brevibacterium flavum AJ 11658, FERM-P 5839, FERM-BP ($Hse^-$, $EG^r$), said culture being capable of producing the aminoacid L-lysine upon aerobic fermentation in an aqueous nutrient medium containing assimilable source of carbon, nitrogen and inorganic substances.

7. A biologically pure culture of a mutant resistant to ethylene glycol identified as Corynebacterium acetoglutamicum AJ 11656, FERM-P 5837, FERM-BP ($AEC^-$, Ala, $EG^-$), said culture being capable of producing the aminoacid L-lysine upon aerobic fermentation in an aqueous nutrient medium containing assimilable sources of carbon, nitrogen and inorganic substances.

* * * * *